United States Patent
Millar et al.

[11] Patent Number: 6,069,688
[45] Date of Patent: *May 30, 2000

[54] METHOD FOR PRODUCING CONTINUOUS IN-LIKE KAPPA MEASUREMENTS FOR PAPERMAKING PULPS

[75] Inventors: Ord D. Millar, Pierrefonds, Canada; Richard J. Van Fleet, Cave Creek, Ariz.

[73] Assignee: Honeywell International Inc., Morristown, N.J.

[*] Notice: This patent is subject to a terminal disclaimer.

[21] Appl. No.: 08/988,971

[22] Filed: Dec. 11, 1997

[51] Int. Cl.[7] .............................. G01N 21/00; G01J 3/30; G01J 3/46
[52] U.S. Cl. .............................. 356/73; 356/318; 356/425
[58] Field of Search .............................. 356/73, 318, 425

[56] References Cited

U.S. PATENT DOCUMENTS

| | | | |
|---|---|---|---|
| 3,994,602 | 11/1976 | Howarth | 356/435 |
| 4,222,064 | 9/1980 | Lodzinski | 356/73 |
| 5,220,172 | 6/1993 | Berthold et al. | 250/461.1 |
| 5,486,915 | 1/1996 | Jeffers et al. | 356/318 |

*Primary Examiner*—Robert H. Kim
*Assistant Examiner*—Zandra V. Smith
*Attorney, Agent, or Firm*—Anthony Miologos

[57] ABSTRACT

A method for the continual, real-time, in-situ generation of a Kappa number used by a process control system to control the delignification of papermaking pulps is disclosed. The method converts a plurality of analog output signals representing the intensities of spectral bands of light energy reflected by the pulp, and feedback analog output signals representing the intensities of spectral bands of light energy before they are injected into the pulp, into digital output values. The digital output values are then normalized in accordance to a normalization algorithm and stored with a time marker. The normalized values are used along with previously-stored coefficient values that represent a model of the delignification process for any particular point in time, and in accordance to the time marker and configuration data from a configuration computer, a Kappa number representation is calculated in accordance to a Kappa number-generating algorithm. The Kappa number representation is then converted into a signal form acceptable by the process control system and used to control the delignification process.

18 Claims, 4 Drawing Sheets

METHOD FOR PRODUCING CONTINUOUS IN-LIKE KAPPA MEASUREMENTS FOR PAPERMAKING PULPS

CROSS-REFERENCE TO RELATED APPLICATIONS

The present application is related to co-pending application, Ser. No. 08/988,972, titled "An Apparatus Used In Determining the Degree of Completion of a Processed Medium"; and co-pending application, Ser. No. 08/989,720, titled "A Continuous In-Line Kappa Measurement System"; both applications filed on the same date herewith, and both applications having a common assignee as the present invention.

FIELD OF THE INVENTION

This invention relates in general to pulp and paper making and more particularly to a method for providing in-situ, and on a real-time basis, the Kappa number representation of the bleachability of papermaking pulps.

BACKGROUND OF THE INVENTION

In the pulp and paper industry, pulping refers to the process of converting wood chip feed stock into separate fibers by the chemical reaction between the lignin found in the wood chips and the active chemicals in a cooking liquor. This delignification process separates the wood cellulose fibers by breaking down the lignin. Lignin is a polymer of complex chemical structure which "cements" together the wood's cellulose fibers. The most prevalent method of delignification is by chemical means in which raw wood chips and chemicals are combined at a controlled pressure and temperature in a vessel known as a digester. While in the digester, the amount of lignin removed from the wood chips determines the product quality, the product yield, and the amount of energy consumed. Fluid drained from the digester during delignification contains lignin removed from the wood chips and is referred to in the industry as "black liquor". Black liquor is subsequently used to advantage during the pulping process as fuel in a boiler to produce process steam.

One common method of delignification presently used in pulp making is the kraft process. In this process, the wood chip feed stock is cooked with caustic soda and sodium sulfide, which removes most of the lignin without attacking the remaining cellulose fibers. When the remaining pulp of the kraft process is not passed through a bleaching process, it is used in cardboard or paper sack production. The dark color of this product is due to the remaining lignin in the fibers. However, if the final product of the process is to be a good-quality white paper, a bleaching step is introduced in the process using chlorine, chlorine dioxide, oxygen, ozone, or hydrogen peroxide as the bleaching agent. The bleaching dissolves the remaining lignin and renders white the remaining cellulose fibers. The amount of whiteness and the term or amount of time that the final paper product remains white are dependent on the remaining residual lignin in the cellulose fibers. It is, therefore, customary to test the lignin content of the pulp fibers and use this determination as a measure of the effectiveness of the ongoing bleaching operation.

Predicting the bleachability of the pulp in the prior art has been by the use of one or more of the several available tests such as the Permanganate Number (TAPPI method T-214), or the Kappa Number (TAPPI method T-236), or the Roe Chlorine Number (TAPPI method 202), etc. Each of these tests is designed to determine the quantity of lignin present in the pulp fibers as a group and provides an indication of the total bleach requirement (the oxidizing agent demand of the pulp) in the bleaching step. The most commonly used of these tests is the Kappa number, which refers to the amount of material remaining in the pulp after cooking that can be oxidized by a standard solution of potassium permanganate. The material is often equated with the lignin content of the fibers.

The Kappa number test, as well as the other tests noted, is most commonly carried out by laboratory analysis of hourly samples of the digester output (samples are typically obtained at the last stage of the brownstock washer). This requires extracting a representative sample of the pulp, separating the pulp fibers from the cooking liquor, drying the pulp to oven-dry conditions, re-suspending the fibers, and treating this new mixture with one or more special agents, all under strict laboratory conditions. The laboratory analysis of the residual lignin takes approximately one hour and, therefore, is a poor method for providing process control feedback and cannot be used for feedforward control. A number of automatic sampling and testing devices have been tried but they have been mostly unsuccessful in providing accurate long-term results and do not reduce the one-hour delay between process and measurement of the residual lignin.

Still other devices are known which use the ultraviolet (UV) fluorescence properties of lignin to measure the lignin concentration. Such testing systems require very dilute lignin solutions to be prepared prior to measurement and, therefore, are not suitable for in-situ, or real-time, testing. Other ultraviolet absorption testing methods have attempted to measure the residual lignin in wood pulp by sampling the pulp every few minutes, preparing and diluting the sample, and circulating the sample into a loop where the UV light absorption is measured over a prescribed time period and the pulp concentration is measured independently. Even though this system provides for a faster method of testing than that of the laboratory method, it is still off-line.

One system known which provides for in-situ lignin testing is taught by U.S. Pat. No. 5,486,915, issued on Jan. 23, 1996, to Jeffers et al. This lignin analyzer uses a fluorescence technique to measure lignin concentration in undiluted samples of wood pulp. This method and apparatus require the use of fairly complex detection methods that use the radiation of the wood pulp with excitation light in a specific wavelength (in the range of 337 nm) in order for the residual lignin in the pulp to emit fluorescence. A spectral distribution of the fluorescence emissions is then determined and output signals produced to a signal processor that quantifies the residual lignin in the pulp by either a wavelength centroid or band ratio method.

Even though this system provides for in-situ, real-time analysis of the lignin concentrations, it is more effective during the early stages of the bleaching process where greater concentrations of lignin are present. In the later stages of the bleaching process the lignin content is reduced appreciably, thereby diminishing the fluorescence emissions of the pulp. This method also does not lend itself to measuring the later stages of the pulp process involving the brightness processing of the pulp, important in the formation of quality paper products requiring a high brightness level. A balance of bleaching agent to brightness must be determined in order not to degrade the strength of the pulp, not increase the cost of the bleaching operation, limit the exposure of personnel to toxic chemicals, and provide minimum impact on the environment.

SUMMARY OF THE INVENTION

Therefore, there is provided by the present invention a method for the continual, real-time, in-situ generation of a Kappa number used by a process control system to control the delignification of papermaking pulps. The method is arranged to be used with an apparatus that injects light energy in a plurality of spectral bands into the pulp and which subsequently collects the light energy reflected by the pulp from at least a first and a second location. The apparatus generates a plurality of first analog output signals indicative of the intensity of each spectral band received from the first location, and a plurality of second analog output signals indicative of the intensity of each spectral band received from the second location, and a plurality of feedback analog output signals indicative of the intensity of each spectral band of light energy injected into the pulp. An included measurement system receives and processes the plurality of first and second analog output signals, the plurality of feedback signals and, with previously-stored first and second coefficient values that represent a model of the delignification process for any particular point in time and configuration data input from a source of configuration data, outputs a Kappa number representation to an output module.

The method of the present invention converts the plurality of first analog output signals, the plurality of second analog output signals, and the plurality of feedback analog output signals into a plurality of first digital output values, a plurality of second digital output values and a plurality of feedback digital output values, respectively. It then uses a normalizing algorithm to generate a first set of normalizing values and a second set of normalizing values that are time marked, using the first, the second and feedback digital output values. The normalized values are used along with the first and second coefficient values, and in accordance to the time marker and configuration data, a Kappa number representation is calculated in accordance to a Kappa number-generating algorithm.

The Kappa number representation is transferred to the output module, where it is converted into a transmission form acceptable by the process control system, whereby the process control system controls the delignification of the papermaking pulp in accordance to the Kappa number representation.

Accordingly, it is an object of the present invention to provide a method for providing in-situ, and on a continual and real-time basis, a Kappa number representation of the bleachability of papermaking pulps.

It is another object of the present invention to provide a method that can produce output signals representing a Kappa number used by a process control system to provide real-time, feed-forward control of the delignification of papermaking pulps.

BRIEF DESCRIPTION OF THE DRAWINGS

Other objects, features, and advantages of the present invention will be apparent from the following description of a preferred embodiment thereof, taken in conjunction with the accompanying drawings, in which.

DETAILED DESCRIPTION OF THE INVENTION

Figure 1:
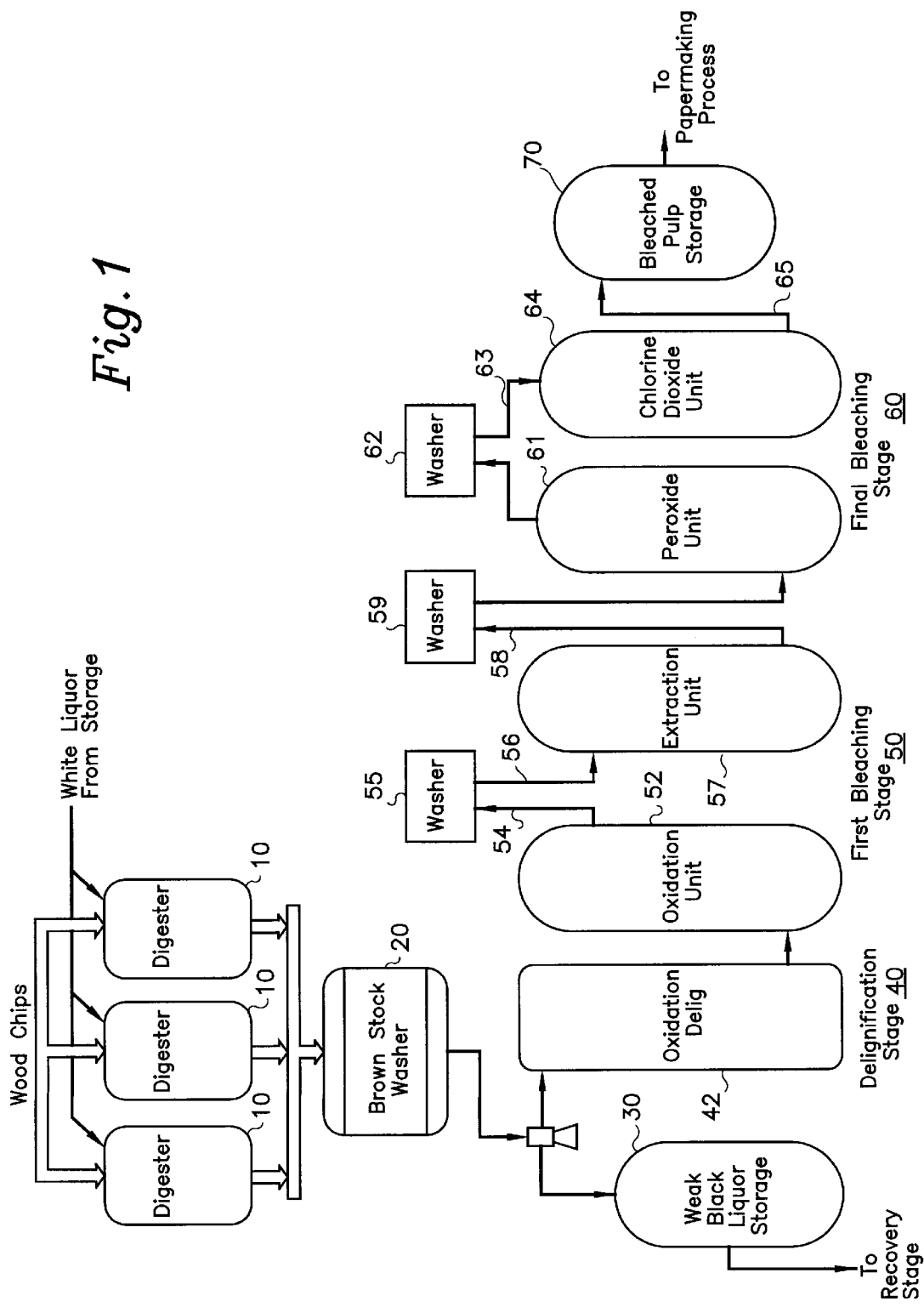
FIG. 1 shows a typical papermaking pulp process where the present invention is used to advantage.

Turning to FIG. 1, a typical process is shown for processing wood chips into papermaking pulp. Wood chips are fed into a plurality of digesters 10 along with a solution known as "white liquor". The white liquor in a kraft process is typically a mixture of sodium hydroxide (NaOH) and sodium sulfide ($Na_2S$). The wood chips and white liquor are cooked in the digesters 10 under controlled temperature and pressure to delignify or extract the binding agent, commonly known as lignin, from the cellulose fibers of the wood chips. Fluid drained from the digesters 10 during the delignification process is called "black liquor" and contains spent white liquor and lignin removed from the wood chips. This black liquor is removed by a one or more "brown stock" washers 20 prior to the pulp bleaching step. The black liquor at this stage is referred to as a "weak" black liquor and consists of sodium sulfate ($Na_2SO_4$), sodium carbonate ($Na_2CO_3$), sodium sulfide ($Na_2S$), and lignin organics. Weak black liquor is normally stored in containers 30 before being fed to a recovery operation.

A key element in the pulping manufacturing process is liquor recovery and power generation. Weak black liquor is fed to a system of multiple effects evaporators (not shown), where it is concentrated. This black liquor is then used as fuel in a furnace to manufacture steam for the papermaking pulp process and for power. A furnace recovery system (not shown) receives the smelt from the recovery furnace, which is dissolved into a "green liquor", clarified, and caustisized with lime and sodium hydroxide (NaOH) to produce white liquor for the pulping process.

When the final product of the pulping process is to be a good-quality white paper, a bleaching process is introduced. The bleaching process varies according to the type of finished product the pulp is to become. Therefore, the number of bleaching stages in the bleaching process and the type of bleaching agents used control the "whiteness" of the finished paper product. Typically, the bleaching process employs a delignification stage 40 and one or more bleaching stages, such as the first bleaching stage 50 and final bleaching stage 60. Each bleaching stage introduces oxygen, chlorine, chlorine dioxide, ozone or some other bleaching agent to the pulp. For this example, the bleaching process begins by feeding the pulp from the brown stock washer 20 to an oxygen ($O_2$) delignification unit 42. This provides further removal of any residual lignin remaining in the pulp after digestion and black liquor removal by the brown stock washer 20. The pulp is then pumped to a first bleaching stage 50, consisting of an oxidation unit 52, a washer 55, and an extraction unit 57. The pulp is pumped to the washer 55 from the oxidation unit 52 via conduit 54 and from the washer 55 to the extraction unit 57 via conduit 56. Oxygen, chlorine dioxide, or other bleaching agents are introduced into the pulp in this stage to further the brightening process. The brightening agents are removed by the extraction unit 57. The pulp is then pumped from the extraction unit 57, via conduit 58, to washer 59 and to peroxide unit 61 of the final bleaching stage 60. From the peroxide unit 61, the pulp is pumped to washer 62 and via conduit 63 to a chlorine dioxide unit 64. Finally, the brightened pulp is piped via conduit 65 to a bleached pulp storage unit 70. The bleached pulp is subsequently used as the raw material in the production of the finished paper product. It will be well understood by those skilled in the art that the bleaching process explained above can consist of more than the three bleaching stages shown in this example and that the present invention can be applied equally to a bleaching process having more than three stages of process.

The bleaching of the pulp dissolves any remaining lignin and renders white the remaining cellulose fibers. The intensity of whiteness and the term that the final paper product remains white are dependent on the remaining residual lignin in the cellulose fibers. It was, therefore, customary in prior art solutions to test either the residual lignin content of the cooking liquors or the pulp during the delignification or bleaching process as a determination of the measure of the effectiveness of the bleaching. The test of the residual lignin content can be used to determine the amount of bleaching agent that must be introduced into the various stages of the process to achieve the required brightness or whiteness of the pulp or, alternatively, the amount of time that the pulp must be kept in the bleaching process to achieve the desired brightness result.

The present invention measures the reflectant qualities of the pulp during the bleaching process, also expressed as the reflectance of the pulp, as the means for determining the remaining lignin and, therefore, the effectiveness of the ongoing bleaching process. The present invention tests the pulp in-situ, continually, on a real-time basis and produces output signals in a form readily understood by those skilled in the art. For example, one of the most widely-used and most reliable measurement standard used in the industry today is the "Kappa number" documented in TAPPI procedure T236 cm-85, "Kappa Number of Pulp". This standard is defined as the number of milliliters of 0.1 normal potassium permanganate ($KMnO_4$) consumed by one gram of unbleached, moisture-free pulp during a specific reaction time under specific conditions. The Kappa number measures the remaining lignin content of the incoming pulp and, therefore, how much work must be done in bleaching.

The Kappa number output signal produced by the present invention can be visually displayed to a human operator via an output device such as an alphanumeric or chart display or printer. Additionally, the Kappa number can be expressed as data, or a process variable, to an automated process control system associated with the bleaching process. The process control system can subsequently control the introduction of bleaching agents to the various delignification and/or bleaching stages in accordance to the measured Kappa number. Additionally, since the measure is continuous, many small adjustments to the bleaching process can be made rather than fewer larger adjustments, leading to a finer, more robust control of the process. Therefore, the present invention monitors the reflectance of the pulp and develops a measurement based on a Kappa number standard to represent the remaining lignin contained by the pulp. The Kappa number can then be used to determine the quantity of bleaching agents that need to be introduced during the bleaching stage of the pulpmaking process to achieve the desired result.

Figure 2:
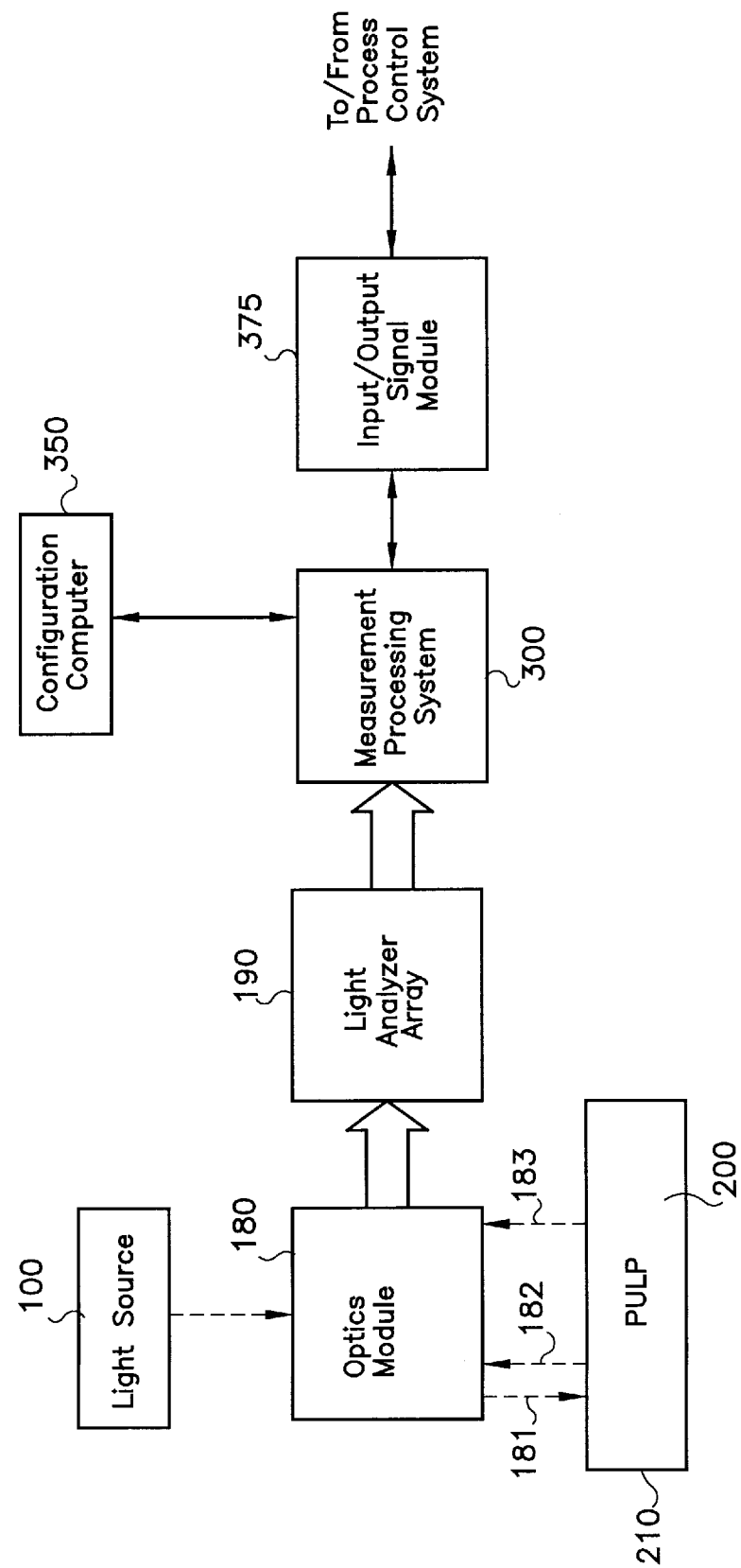
FIG. 2 is a schematic block diagram of the Kappa measurement system of the present invention.

Turning now to FIG. 2 of the included drawings, a schematic block diagram of a Kappa measurement system is illustrated. The system includes an optics module 180 that receives light energy from a light source 100. Light source 100 produces and emits light energy composed of a plurality of wavelengths. Optics module 180 injects the light energy into the pulp 200 which is conveyed within a conduit 210. The light energy reflected by the pulp 200 is collected by optics module 180 and transmitted to light analyzer 190. Light analyzer 190 analyzes the collected light energy and produces output signals representing the intensity of each wavelength collected. The wavelength intensities are next transmitted to a measurement processing system 300, where the reflectance data is processed along with previously-stored coefficient values, representing a model of the delignification process, and offsets, gains, or other tuning data entered via configuration computer 350. The measurement processing system 300 uses preprogrammed algorithmic formulae to translate the collected wavelength intensities and user-input data into a Kappa number representation. The resultant Kappa number representation is output to an input/output signal module 375. The signal module 375 converts the Kappa number from the measurement processing system into an output signal that can be read by a process control system. For example, module 375 can convert the Kappa number representation into a 4 mA-to-20 mA current loop output that is commonly used in the process control industry to pass control variable information from field devices to a controller. Alternatively, the data can be output as serial or parallel digital data to a data network for transmission to the process control system. It will be well understood to those skilled in the art that the Kappa number representation output by module 375 can be converted into any one of a number of presently-known communication methods employed between field devices and processing systems and used for exchanging information and data.

With renewed reference to FIG. 2, a more detailed explanation of the Kappa measurement system will be made. Light energy having at least the blue, green, amber and infrared wavelengths is produced and emitted by a light source 100 and injected into the pulp 200, or an undiluted sample of pulp at a location shown by arrow 181. The light source 100 can be a quartz halogen bulb, or any one of the many devices known by those skilled in the art, that can produce and emit light energy in at least the above-mentioned spectra of wavelengths. The pulp 200 is typically conveyed through a pipe or conduit 210 that forms a part of the overall plant bleaching process. For example, with renewed reference to FIG. 1, the present invention can be used to sample the pulp flowing in conduit 44 after the $O_2$ delignification unit 42, or in conduit 54 after oxidation unit 52. Alternatively, conduit 210 can comprise a bypass line from any of the aforementioned bleaching process conduits that convey a portion of the total pulp taken from the conduits.

Some of the injected light energy is absorbed by the pulp and some reflected (thus it is re-radiated) correlating to the pulp properties. The light energy reflected by pulp 200 is collected at two different locations. One location 182 is near the point of injection and the second location 183 is farther from the point of injection 181. The reflected light energy collected by optics module 180 is passed to light analyzer array 190. Light analyzer array 190 includes a near-light analyzer and a far-light analyzer (not shown). Each analyzer receives the reflected light from the respective near- and far-light collectors of optics module 180. Each analyzer detects, measures and produces analog output signals representing the intensity of each wavelength of light energy reflected by the pulp 200. That is, each analyzer produces an individual analog output signal representing the intensity of the blue, green, amber and infrared wavelengths collected.

In order to provide a baseline of the intensity of each wavelength produced by the light source 100, the present invention includes a light source feedback arrangement. The light energy produced by light source 100 and applied to optics module 180 is shunted before injection into the pulp 200 and delivered to the light analyzer array 190. The light analyzer array further includes a feedback-light analyzer (not shown) that detects, measures and produces analog output signals representing the intensity of each of the blue, green, amber and infrared wavelengths of light energy emitted by the light source 100. The feedback arrangement can also be used to ascertain a drop-off of the light energy intensity produced by light source 100, due to its failure or imminent failure.

A detailed understanding of the optics module 180 and light analyzer 190 as well as the means used in converting the collected and feedback light into output signal representations may be had by reference to applicants' co-pending application, Ser. No. 08/988,972, titled, "An Apparatus Used in Determining the Degree of Completion of a Processed Medium", and co-pending application, Ser. No. 08/989,720, titled "A Continuous In-Line Kappa Measurement System"; which co-pending applications are incorporated herein by reference.

Figure 3:
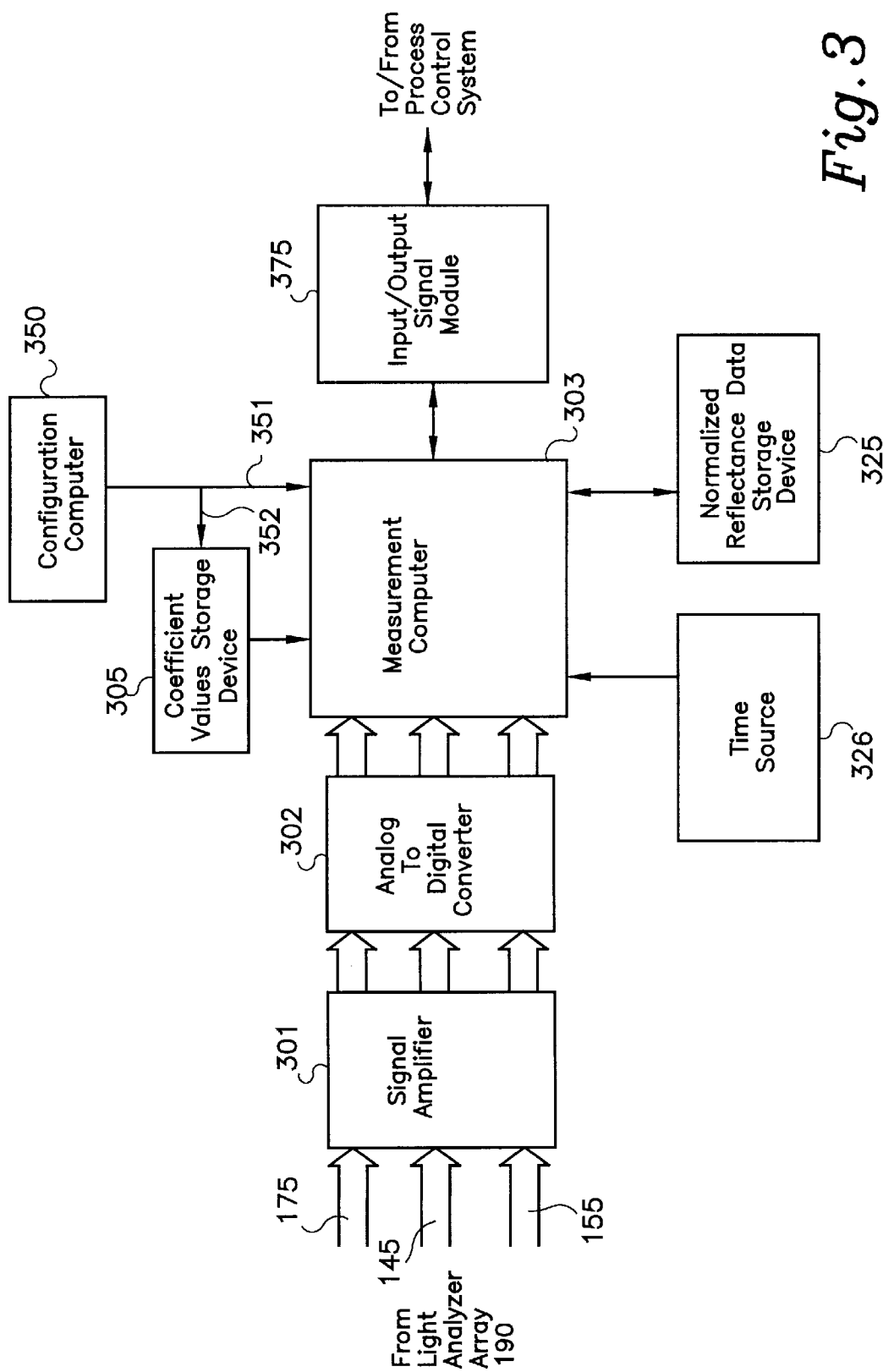
FIG. 3 is a schematic block diagram of the measurement processing system in accordance to the present invention.

Turning now to FIG. 3 of the included drawings, the major components of the measurement processing system 300 are shown. Analog voltage signals 145, 155 and 175 corresponding to analog output signals generated by the near-light, far-light and feedback-light analyzers respectively, of light analyzer array 190, are connected to signal amplifier 301 where they are amplified. The signals are then output to an analog-to-digital converter 302, where they are digitized into a matrix of sensed component values. The digitized component values representing the near- and far-light reflection intensities and feedback-light intensities are next applied to measurement computer 303, where they are processed. Stored within measurement computer 303 is an operating system and conversion algorithms that act on the component values received from analog-to-digital converter 302.

Figure 4:
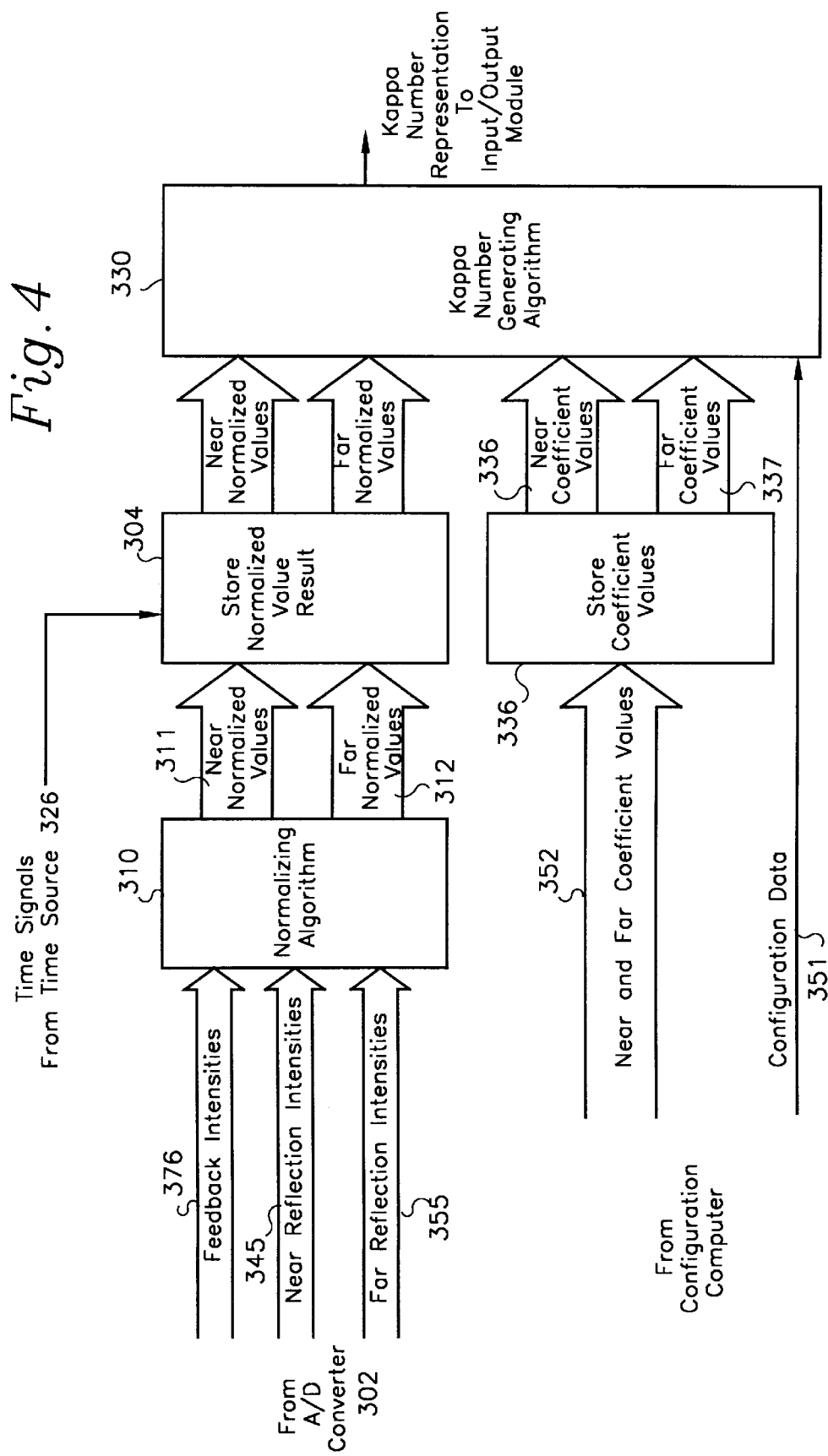
FIG. 4 is a block diagram of the method used by the measurement processing system to calculate the Kappa number representation in accordance to the present invention.

As can be seen in FIG. 4, the digital values of near-reflection intensities 345, far-reflection intensities 355 and feedback intensities 376 are first normalized by a normalizing algorithm shown by block 310. The normalizing algorithm 310 divides each wavelength of the near-reflection intensities 345 and each wavelength of the far-reflection intensities 355 by a respective wavelength of the feedback intensities 376.

The mathematical relationship for the normalization is:
$Nx/Fx = Vnx$ (for the near-reflection intensities 345)
$FRx/Fx = Vfrx$ (for the far-reflection intensities 355)
where:
x=one of the blue, green, amber and infrared wavelengths;
Nx=the intensity of the x wavelength of the near-reflection intensities;
Fx=the intensity of the x wavelength feedback signal;
Vnx=the resultant normalized value for the specific near-x wavelength;
FRx=the intensity of the x wavelength of the far-reflection intensities; and
Vfrx=the resultant normalized value for the specific far-x wavelength.

A normalized reflectance value is calculated for each near wavelength 311 and each far wavelength 312 and the values stored (block 304) in a normalized reflectance data storage device 325 along with a time stamp or marker from a time source 326 of the time when the wavelengths where collected. The source of time signals 326 can be any device or scheme that will output an accurate signal representing the chronological time.

A set of coefficient values is stored (block 335) in a coefficient value storage device 305. The coefficient values are also time stamped. This set of coefficient values includes a value for each near and far wavelength that the system of the present invention processes. The coefficient values are derived from detailed laboratory analysis of the particular pulping or bleaching process and a process history. In other words, the coefficient values stored in the coefficient value storage device 305 comprise a set of constant values that represent a model of the "ideal" values for each reflected wavelength received at a particular point in time of the process. The coefficient values are used with the normalized reflectance values to calculate the Kappa number representation.

Overall system gain (G) and offset value or bias (O) are entered into measurement computer 303 by a configuration computer 350. Configuration computer 350 can be connected directly to the measurement computer by a serial or parallel data line 351, or alternatively, located remote from the measurement computer 303. For a remotely-located configuration computer, line 351 may be replaced by any of the known methods for establishing a remote communications link between two or more computing devices. The data transmitted from the configuration computer 350 to the measurement computer 303 allows the fine tuning of the resultant Kappa number generation based on the particularity of the bleaching process, process history and prior laboratory sample comparisons. Similarly, the configuration computer 303 downloads either directly or remotely the near and far coefficient values to the coefficient values storage device 305 via a transmission path shown generally as 352.

The Kappa number-generating algorithm shown by block 330 receives the near normalized values 311 and far normalized values 312 from storage device 325, representation is derived using the normalized reflectance values stored in data storage device 325, the near coefficient values 336 and far coefficient values 337 stored in the coefficient values storage device 305, for a specific point in time, and the configuration data. The normalized reflectance values 311 and 312 stored in device 325, with a specific time stamp or marker, are processed with only the coefficient values contained in storage device 305 that have a like time stamp. For example the normalized reflectance values stored at 10:00 a.m. are calculated with coefficient values stored in device 305 that are time stamped to be used with normalized reflectance values collected at 10:00 a.m. For any particular point of time, the system uses the following algorithm routine to calculate the Kappa number:

(KnbVnb+KngVng+KnaVna+KnirVnir+KfrbVfb+ KfrgVfrg+KfraVfra+KfrirVfrir) * G+O where:
 Knb=the near coefficient value for the blue wavelength;
 Vnb=the normalized near blue wavelength received;
 Kfrb=the far coefficient value for the blue wavelength;
 Vfrb=the normalized far blue wavelength received;
and where;
 b=blue wavelength;
 g=green wavelength;
 a=amber wavelength; and
 ir=infrared wavelength.

The result of the above-identified algorithm is a Kappa number representation of the bleachability of the pulp. The Kappa number value calculated by block 330 of measurement computer 303 is output to input/output module 375 and converted into one of the above-mentioned output signal types for output to a display, a chart recorder, printer, or process control system. Ideally, the Kappa number is transmitted to a process control system to control the delignification or the amount of bleaching agents introduced to the pulping process in order to achieve the desired finished paper product.

It will be appreciated by those skilled in the art that the process control system can also be used to enter the gain or offset values via the input/output signal module. Additionally, the measurement computer can include a data-logging capability tasked in recording and storing the raw wavelength data or processed Kappa number over a period of time. This data can then be downloaded to the process control system via the input/output signal module for modeling, process history analysis or comparison with laboratory samples.

The present invention has been described with particular reference to the preferred embodiments thereof. It will be obvious that various changes and modifications can be made therein without departing from the spirit and scope of the invention as defined in the appended claims that characterize a method for the continual, real-time, in-situ generation of a Kappa number used by a process control system to control the delignification of papermaking pulps that converts a plurality of analog output signals representing the intensities of spectral bands of light energy reflected by the pulp, and feedback analog output signals representing the intensities of spectral bands of light energy before they are injected into the pulp, into digital output values. The digital output values are then normalized in accordance to a normalization algorithm. The normalized values are used along with previously-stored coefficient values that represent a model of the delignification process for any particular point in time, and in accordance to the time marker and configuration data from a configuration computer, a Kappa number representation is calculated in accordance to a Kappa number-generating algorithm. The Kappa number representation is then converted into a signal form acceptable by the process control system and used to control the delignification process.

What is claimed is:

1. A method for the continual, real-time, in-situ generation of a Kappa number used by a process control system to control the delignification of papermaking pulps, said method arranged to be used with an apparatus that includes a light source for generating light energy in a plurality of wavelengths, an optics module connected to said light source for injecting said light energy into said pulp and subsequently collecting said light energy reflected by said pulp from a first and a second location, a feedback device connected to said light source and associated with said optics module arranged to return said light energy from a location proximate said optics module and a light analyzer array connected to said optics module arranged to receive said reflected light energy collected by said optics module from said first and second locations and said light energy returned by said feedback device, said light analyzer array arranged to determine the intensity of each wavelength of light energy received from each of said first and second locations and from said feedback device and to generate a plurality of first analog output signals indicative of the intensity of each wavelength received from said first location, a plurality of second analog output signals indicative of the intensity of each wavelength received from said second location, and a plurality of feedback analog output signals indicative of the intensity of each wavelength received from said feedback device, said apparatus further including a measurement processing system, a configuration device connected to said measurement processing system for providing at least a first set and a second set of coefficient values and configuration data to said measurement processing system, and an output module connected to said measurement processing system and said process control system, the method comprising the steps of:

retrieving said first set and said second set of coefficient values from said configuration device and storing said first and second set of coefficient values in first storage means;
 connecting said plurality of first analog output signals, said plurality of second analog output signals and said plurality of feedback analog output signals to said measurement processing system;

converting said plurality of first analog output signals, said plurality of second analog output signals and said plurality of feedback analog output signals into a plurality of first digital output values, a plurality of second digital output values and a plurality of feedback digital output values respectively;

normalizing said plurality of first digital output values and said second plurality of digital output values and generating a first set of normalized values and a second set of normalized values respectively;

storing said first set and said second set of normalized values in second storage means;

retrieving said first and second set of coefficient values from said first storage means, said first and second set of normalized values from said second storage means, and generating a Kappa number representation using said first and second set of coefficient values, said first and second set of normalized values and said configuration data;

transferring said Kappa number representation to said output module; and converting said Kappa number representation into a transmission form acceptable by said process control system, whereby said process control system controls the delignification of said papermaking pulp in accordance to the Kappa number representation.

2. The method as claimed in claim 1, wherein there is further included the step of:

amplifying said plurality of first analog output signals, said plurality of second analog output signals and said plurality of feedback analog output signals before the step of converting.

3. The method as claimed in claim 1, wherein measurement processing system further includes a source of time signals and said step of normalizing divides each of the respective wavelength intensities of said plurality of first digital output values by a respective one of the wavelength intensities of said plurality of feedback digital output values, thereby producing said first set of normalized values; and said step of normalizing further divides each of the respective wavelength intensities of said plurality of second digital output values by a respective one of wavelength intensities of said plurality of feedback digital output values and stores said first and said second normalized values in said second storage means with a time marker from said source of time signals.

4. The method as claimed in claim 3, wherein said step of normalizing is implemented as an algorithm preprogrammed into said measurement processing system.

5. The method as claimed in claim 4, wherein said configuration device is a configuration computer connected locally or, alternatively, remotely to said measurement processing system and said configuration data comprises at least system gain (G) and offset bias (O).

6. The method as claimed in claim 5, wherein said first set and said second set of coefficient values include coefficient values that are related to a specific point in time, and the generation of said Kappa number representation includes the steps of:

multiplying a respective one of said first set of coefficient values for a specific point in time to a respective and associated one of said first normalized values having a corresponding point in time defined by said time marker thereby producing a first set of products, and multiplying a respective one of said second set of coefficient values for a specific point in time to a respective and associated one of said second normalized values having a corresponding point in time defined by said time marker thereby producing a second set of products;

summing said first set of products, producing a first sum;

summing said second set of products, producing a second sum;

summing said first and second sums, producing a total;

multiplying said total by the system gain (G); and adding the offset bias (O).

7. The method as claimed in claim 6, wherein the generation of said Kappa number representation is implemented as an algorithm preprogrammed into said measurement processing system.

8. The method as claimed in claim 1, wherein said step of converting converts said Kappa number representation into a 4 mA-to-20 mA current loop.

9. The method as claimed in claim 1, wherein said step of converting converts said Kappa number representation into serial or parallel formatted digital data.

10. The method as claimed in claim 1, wherein said step of converting converts said Kappa number representation into an output signal compatible with display, charting or printing devices.

11. A method for the continual, real-time, in-situ generation of a Kappa number used by a process control system to control the delignification of papermaking pulps, said method arranged to be used with an apparatus that injects light energy in a plurality of spectral bands into the pulp and subsequently collects said light energy reflected by said pulp from a first and a second location, generating a plurality of first analog output signals indicative of the intensity of each spectral band received from said first location, and a plurality of second analog output signals indicative of the intensity of each spectral band received from said second location, said apparatus further providing a plurality of feedback analog output signals indicative of the intensity of each spectral band of light energy injected into said pulp, a source of coefficient values and configuration data, a measurement system for receiving and processing said plurality of first and second analog output signals, said plurality of feedback signals and said configuration data, and an output module connected to said measurement system and said process control system, the method comprising the steps of:

retrieving a first set and a second set of coefficient values from said source of coefficient values;

converting said plurality of first analog output signals, said plurality of second analog output signals and said plurality of feedback analog output signals into a plurality of first digital output values, a plurality of second digital output values and a plurality of feedback digital output values, respectively;

generating a first set of normalized values and a second set of normalized values using said plurality of feedback digital output values;

generating a Kappa number representation using said first and said second set of coefficient values, said first and second set of normalized values and said configuration data;

transferring said Kappa number representation to said output module; and converting said Kappa number representation into a transmission form acceptable by said process control system, whereby said process control system controls the delignification of said papermaking pulp in accordance to the Kappa number representation.

12. The method as claimed in claim 11, wherein there is further included the step of: amplifying said plurality of first analog output signals, said plurality of second analog output signals and said plurality of feedback analog output signals before the step of converting.

13. The method as claimed in claim 11, wherein measurement processing system further includes a source of time signals and said step of normalizing divides each of the respective wavelength intensities of said plurality of first digital output values by a respective one of the wavelength intensities of said plurality of feedback digital output values, thereby producing said first set of normalized values; and said step of normalizing further divides each of the respective wavelength intensities of said plurality of second digital output values by a respective one of wavelength intensities of said plurality of feedback digital output values and stores said first and said second normalized values in said second storage means with a time marker from said source of time signals.

14. The method as claimed in claim 13, wherein said step of generating coefficient values is implemented as an algorithm preprogrammed into said measurement system.

15. The method as claimed in claim 14, wherein said source of configuration data is a configuration computer connected locally or, alternatively, remotely to said measurement system providing configuration data comprising of at least system gain (G) and offset bias (O).

16. The method as claimed in claim 15, wherein said first set and said second set of coefficient values include coefficient values that are related to a specific point in time, and the generation of said Kappa number representation includes the steps of:

multiplying a respective one of said first set of coefficient values for a specific point in time to a respective and associated one of said first normalized values having a corresponding point in time defined by said time marker thereby producing a first set of products, and multiplying a respective one of said second set of coefficient values for a specific point in time to a respective and associated one of said second normalized values having a corresponding point in time defined by said time marker thereby producing a second set of products;

summing said first set of products, producing a first sum;

summing said second set of products, producing a second sum;

summing said first and second sums, producing a total;

multiplying said total by the system gain (G); and adding the offset bias (O).

17. The method as claimed in claim 16, wherein the generation of said Kappa number representation is implemented as an algorithm preprogrammed into said measurement system.

18. The method as claimed in claim 11, wherein said plurality of spectral bands are comprised of at least the blue, green, amber and infrared wavelengths.

* * * * *

UNITED STATES PATENT AND TRADEMARK OFFICE
CERTIFICATE OF CORRECTION

PATENT NO: 6,069,688

DATED: May 30, 2000

INVENTOR(S): Ord D. Millar, Richard J. Van Fleet

It is certified that an error appears in the above-identified patent and that said Letters Patent are hereby corrected as shown below:

In the Title, delete IN-LIKE and insert therefor

-- IN-LINE --

Signed and Sealed this

Twenty-fourth Day of April, 2001

Attest:

NICHOLAS P. GODICI

Attesting Officer

Acting Director of the United States Patent and Trademark Office